US012754124B2

(12) United States Patent
Du

(10) Patent No.: US 12,754,124 B2
(45) Date of Patent: Oct. 6, 2026

(54) HEMATOLOGICAL PARAMETER FOR VIRAL INFECTION

(71) Applicant: Beckman Coulter, Inc., Brea, CA (US)

(72) Inventor: Yuxiao Du, Beijing (CN)

(73) Assignee: Beckman Coulter, Inc., Brea, CA (US)

( * ) Notice: Subject to any disclaimer, the term of this patent is extended or adjusted under 35 U.S.C. 154(b) by 988 days.

(21) Appl. No.: 17/920,152

(22) PCT Filed: Apr. 19, 2021

(86) PCT No.: PCT/CN2021/087984
§ 371 (c)(1),
(2) Date: Oct. 20, 2022

(87) PCT Pub. No.: WO2021/213291
PCT Pub. Date: Oct. 28, 2021

(65) Prior Publication Data

US 2023/0160804 A1 May 25, 2023

(30) Foreign Application Priority Data

Apr. 21, 2020 (CN) ........................ 202010319750.0

(51) Int. Cl.

| | |
|---|---|
| ***G01N 15/01*** | (2024.01) |
| ***G01N 15/1031*** | (2024.01) |
| ***G01N 15/1404*** | (2024.01) |
| ***G01N 15/1434*** | (2024.01) |
| ***G01N 33/49*** | (2006.01) |
| ***G16H 50/20*** | (2018.01) |

(52) U.S. Cl.
CPC ..... *G01N 15/1404* (2013.01); *G01N 15/1031* (2013.01); *G01N 15/1434* (2013.01); *G01N 33/4915* (2013.01); *G16H 50/20* (2018.01); *G01N 15/01* (2024.01)

(58) Field of Classification Search
None
See application file for complete search history.

(56) References Cited

U.S. PATENT DOCUMENTS

2019/0324035 A1 10/2019 Magari et al.

FOREIGN PATENT DOCUMENTS

| | | |
|---|---|---|
| CN | 108604466 A | 9/2018 |
| CN | 110031614 A | 7/2019 |
| JP | 2019-504992 A | 2/2019 |

OTHER PUBLICATIONS

Giuseppe, Lippi et al., The Critical Role of Laboratory Medicine During Coronavirus Disease 2019 (COVID-19) and other Viral Out Breaks, Clinical Chemistry Laboratory Medicine, Mar. 19, 2020, 58(7), pp. 1063-1069.

Notice of Reasons for Rejection for Japanese Patent Application No. 2022-563133, dated Feb. 14, 2025, 3 pages.

Chaves F, Tierno B, Xu D. "Quantitative Determination of Neutrophil VCS Parameters by the Coulter Automated Hematology Analyzer: New and Reliable Indicators for Acute Bacterial Infection." American Journal of Clinical Pathology 2005; 124-440-4.

Chaves, F, Tierno B, Xu D. "Neutrophil Volume Distribution Width: A New Automated Hematologic Parameter for Acute Infection." Archive Pathology and Laboratory Medicine 2006; 130:378-380.

Chan, F, Yuan S, Kok KH et al. "A Familial Cluster of Pneumonia Associated with the 2019 Novel Coronavirus Indicating Person to Person Transmission: A Study of a family Cluster." Lancet. 2020,395 (10223):514-523.

Frater, John L. et al.: "Covid-19 and The Clinical Hematology Laboratory", International Journal of Laboratory Hematology, [Online] vol. 42, No. S1, Apr. 20, 2020, pp. 11-18, XP055816538, GB; US ISSN: 1751-5521, DOI: 10.1111/ijlh.13229 Retrieved from the Internet: URL:https://onlinelibrary.wiley.com/doi/fu11-xml/10.1111/ijlh.13229>[retrieved on Mar. 27, 2024].

Huang, C, Wang Y, Li X, Ren L Zhao J, Hu Y, Zhang L et al. "Clinical Features of Patients Infected with 2019 Novel Coronavirus in Wuhan, China." Lancet 2020; 395:497-506.

Pan Y, Guan H, Zhou S, Wang Y, Li Q, Zhu T et al. "Initial CT Findings and Temporal Changes in Patients with the Novel Coronavirus Pneumonia (2019-nCoV): a study of 63 patients in Wuhan, China." European Radiology. 2020. S00330-020-06731-x.

Rai, Sharada et al: "Utility of DxH 800 VCS Parameters and Lymph Index in Predicting Dengue", Journal of Clinical and Diagnostic Research [Online] Jan. 1, 2019 (Jan. 1, 2019), XP093146184, ISSN: 2249-782X, DOI: 10.7860/JCDR/2019/38500.13044, Retrieved from the Internet: URL:https//www.researchgate.net/pubication/335162766_Utility_of_DxH_800_VCS_Parameters_and_Lymph_Index_in_Predicting_Dengue/fulltext/5e7b577f92851cdfca2fa43f/Utility-of-DxH-800-VCS-Parameters-and-Lymph-Index-in-Predicting-Denue.pdf>, [retrieved on Mar. 27, 2024].

Tan W, Zhao X, Ma X et al. "A Novel Coronavirus Genome Identified in a Cluster of Pneumonia Cases—Wuhan, China" 2019-2020. N. Engl J. Med Feb. 20, 2020; 382(8): 727-733.

Xu D. "Clinical Applications of Leukocyte Morphological Parameters." Int J. Clin Res. 2015; 1:1.

Yan, Yufei et al. "Role of Neutrophil/Lymphocyte Ratio in Covid-19" (Laboratory Medicine), Apr. 14, 2020 pp. 1-7.

Zhu Y, Cao X, Xu D. "Detection of Morphologic Changes in Peripheral Mononuclear Cells in Hepatitis B Virus Infection using the Beckman Coulter DXH 800." Laboratory Hematology 2011, 17:22-26.

(Continued)

*Primary Examiner* — Michael D Burkhart
(74) *Attorney, Agent, or Firm* — FBT Gibbons LLP; Nicole M. Tepe

(57) ABSTRACT

The disclosure relates to hematological parameters of viral infection. More specifically, the present disclosure relates to automated volume biomarkers lymph index and monocyte distribution width (MDW) for early detection of Coronavirus infection. The invention also relates to a method, device and computer executable program for early diagnosis of SARS-CoV-2 infection using volume biomarker lymph index and monocyte distribution width (MDW). According to some technical solutions of the present invention, the automated volumetric parameter lymph index and MDW can be used as viral biomarkers to help healthcare workers in the out-patient department or fever clinic to rapidly identify those who might be infected with SARS-CoV-2 and to provide valuable information for triage decision making.

15 Claims, 2 Drawing Sheets

(56) References Cited

OTHER PUBLICATIONS

Zhu Y. et al: "The Lymph Index: A Potential Hematological Parameter for Viral Infection", International Journal of Infectious Diseases, vol. 17, No. 7, Jul. 1, 2013 (Jul. 1, 2013), pp. e490-e493, XP093146167, CA ISSN: 1201-9712, DOI: 10.1016/j.ijid.2012.12.002.

HEMATOLOGICAL PARAMETER FOR VIRAL INFECTION

CROSS-REFERENCE TO RELATED APPLICATIONS

This application is a national phase application of PCT/CN2021/087984, filed on 19 Apr. 2021, which claims priority to Chinese application number 202010319750.0, filed on 21 Apr. 2020. The entirety of each of the aforementioned applications is incorporated by reference herein.

FIELD

The present invention relates to the detection of viral infections, especially the detection of Coronavirus infections, especially the early detection of Coronavirus infections.

BACKGROUND

In December 2019, a pneumonia epidemic of unknown cause broke out in Wuhan, China. Subsequent deep sequencing analysis of lower respiratory tract samples showed that the pathogen was a new coronavirus [1].

Coronavirus, belonging to the Nidovirales, Coronaviridae, Coronavirus genus, is a type of RNA virus with an envelope and a linear single-stranded positive strand as the genome, and is a large class of viruses widely existing in nature. The genome of Coronavirus has a methylated cap structure at the 5' end and a poly (A) tail at the 3' end, and a full-length of about 27-32 kb, which is the largest among the genome of known RNA viruses. Six subtypes of Coronaviruses (HCoV-229E, HCoV-OC43, SARS-CoV, HCoV-NL63, HCoV-HKU1, and MERS-CoV) have been known to infect humans. Among them, 229E, NL63, OC43 and HKU1 usually cause mild or moderate upper respiratory tract diseases such as cold, while SARS-CoV and MERS-CoV can cause serious fatal diseases. The pathogen causing the outbreak of pneumonia in Wuhan is the seventh subtypes of Coronavirus confirmed to infect humans. Studies have shown that its genetic structure is 82% similar to SARS-CoV [2]. Based on this similarity, the International Committee on Taxonomy of Viruses (ICTV) named the virus as Severe Acute Respiratory Syndrome Coronavirus Type 2 (SARS-CoV-2), and the World Health Organization (WHO) named the pneumonia disease as Coronavirus Disease 2019 (COVID-19).

Currently, COVID-19 has been declared a global pandemic by WHO and has spread to more than 100 countries. As of March 2020, the total number of patients in the world has reached 900,000, the number of deaths has exceeded 40,000, and these numbers are still increasing rapidly. Recent studies revealed that SARS-CoV-2 could transmit among human, mainly through respiratory droplets [3]. The incubation period is generally 3-7 days, up to 14 days. The main symptoms (low fever, fatigue, and dry cough) are usually mild and non-specific, which make it difficult to identify infected individuals early or in the incubation period.

Although several laboratory tests, such as lymphocyte count, C-reactive protein, chest imaging studies or molecular testing [4], have been used to aid diagnosis of Coronavirus, they are neither specific nor sensitive or not widely available. At present, the diagnostic standard commonly used in various countries is to perform nucleic acid specific detection on patient samples (such as nasal swabs), but such method generally has the disadvantages of poor repeatability, insufficient sensitivity (especially in the early stage of infection), inaccurate sampling, and high requirements for technical personnel.

From an epidemiological point of view, it is important to identify infected individuals with high sensitivity early in the infection. Especially for individuals who are in close contact with patients with known COVID-19 or who are in epidemic areas, early screening and diagnosis can provide valuable information for timely and effective medical observation and intervention, triage decisions, and even control decisions in disease endemic areas. In the current diagnosis of COVID-19, a patient with the contact history, clinical symptoms, CT image resembling viral infection and positive molecular testing is generally determined as a confirmed case, while whose with contact history, clinical symptoms, CT image resembling viral infection and negative molecular testing on admission are determined as suspected cases. The disadvantage is that there is a lag in the detection of nucleic acid molecules (an important marker of COVID-19 diagnosis), which is not desirable for early screening of the disease. The reason may be that the viral load in the early stage of the disease is low, making it difficult to obtain high-sensitivity results through nucleic acid molecule detection. This makes it difficult to carry out early identification, classification, and therapeutic intervention for "suspected" individuals, and even leads to the further spread of the disease due to lack of timely isolation. Therefore, there is an urgent need to find a way to quickly identify patients who may be infected, especially in the early stages of infection, so as to provide valuable information for triage decisions.

SUMMARY

Modern automated hematology analyzer with VCS (volume, conductivity, and light scatter) technology can determine the intrinsic biophysical properties of over 8000 peripheral leukocytes in their 'near in vivo state'. VCS technology uses direct current impedance for the cell volume, radio frequency opacity to evaluate conductivity for cytoplasmic chemical composition and nuclear volume, and a laser beam to measure multiple angles of light scatter for cell surface topography, cytoplasmic granularity and nuclear structure. It can also measure the degree of cell volume variation. These morphometric measurements are known as cell population data (CPD). The inventor found that, dynamic changes in volumetric parameters of circulating activated mononuclear cells in response to SARS-CoV-2 infection could be quantitatively determined by automated hematology analyzer and would serve as useful biomarkers for rapidly screening those suspected individuals who have been in close contact with known COVID-19 patients or in epidemic region for likely infection.

The present disclosure relates to volume biomarkers for early diagnosis of Coronavirus infections, such as monocyte distribution width (MDW), lymphocyte volume (LV), lymphocyte distribution width (LV-SD), lymphocyte conductivity (LC), lymph Index, mean neutrophil volume (MNV), neutrophil distribution width (NDW). The invention also relates to a method, device and computer executable program for the early diagnosis of Coronavirus infection using such biomarkers. According to some technical solutions of the present invention, the automated volume parameter lymph index and MDW can be used as viral biomarkers to help healthcare workers in the out-patient department or fever clinic to rapidly identify those who might be infected with COVID-19 and to provide valuable information for triage decision making.

In the study, the inventors surprisingly found that for those patients suspected of early COVID-19 who have not been diagnosed, the dynamic changes in volumetric parameters of circulating activated mononuclear cells in response to SARS-CoV-2 infection could be quantitatively determined by automated hematology analyzer and would serve as useful biomarkers for rapidly screening. The inventors demonstrated that some cell population data, especially the lymph index and monocyte distribution width (MDW) were significantly increased in COVID-19 patients. With designated cutoff values for lymph index and MDW, we achieved the sensitivities of 84.4% and 78.1%, respectively in diagnosing COVID-19 infection. In addition, lymph index in combination with MDW demonstrates excellent diagnostic performance (AUC of 0.83, higher that the AUC of 0.77 with MDW alone and the AUC of 0.79 with lymph index alone). This shows that the combination of MDW and lymph index can more truly reflect the possibility of the subject suffering from SARS-CoV-2 infection, compared with MDW or lymph index alone. Furthermore, we show that lymph index and MDW in suspected patients, like confirmed patients were also significantly increased at the time of admission, suggesting similar pathophysiological process. In particular, 89% of the suspected patients with positive test according to this protocol (with negative nucleic acid molecule test) were diagnosed with COVID-19 during the subsequent disease course. This illustrates clinical significance that lymph index and MDW can be used as sensitive screening biomarkers to rapidly identify those suspected individuals before nuclear acid confirmation and to develop proper management plan.

One aspect of the invention relates to a method for identifying a subject having a viral infection, the method comprising:

1) flowing a body fluid sample obtained from the subject through a flowcell;
2) measuring individual cells of the plurality of cells in the body fluid sample;
3) determining one or more cell population parameter data values in the body fluid sample based on the measuring, wherein the one or more cell population parameter data values comprise a population parameter data value from one or more of lymphocyte, neutrophil and monocyte; and
4) determining whether or not at least one of the one or more cell population data values exceeds a predetermined threshold, wherein if at least one of the one or more cell population parameter values exceeds a predetermined threshold, the viral infection in the subject is indicated.

In an embodiment of this aspect, the viral infection is associated with upper respiratory tract illnesses. In a preferred embodiment, the viral infection is Coronavirus infection. In a more preferred embodiment, the Coronavirus is SARS-CoV-2. In an embodiment, the upper respiratory tract illness is COVID-19.

In an embodiment, the cell population data comprises one or more selected from the group consisting of monocyte distribution width (MDW), lymphocyte volume (LV), lymphocyte distribution width (LV-SD), lymphocyte conductivity (LC), lymph index, mean neutrophil volume (MNV), neutrophil distribution width (NDW), or any combinations thereof. In a preferred embodiment, the cell population data comprises MDW, and one or more of lymph index and LV-SD. In a preferred embodiment, the cell population data comprises a combination of two or more selected from the group consisting of MDW, LV, LV-SD, LC, and lymph index. In a preferred embodiment, the cell population data is a combination of MDW and one or more of LV, LV-SD, LC and lymph index. In a more preferred embodiment, the cell population data consists of MDW and lymph index. In another embodiment, the cell population data comprises or consists of MNV and NDW. The lymph index is calculated according to lymph index=LV×(LV-SD)/LC.

In an embodiment, if one or more of the cell population data exceeds a predetermined threshold, the viral infection in the subject is indicated.

In an embodiment, if the value of the MDW is greater than 20.27, the viral infection in the subject is indicated. In a preferred embodiment, if the value of the MDW is greater than 20.42, the viral infection in the subject is indicated. In a more preferred embodiment, if the value of the MDW is greater than 20.73, the viral infection in the subject is indicated. In an even more preferred embodiment, if the value of the MDW is greater than 21.24, the viral infection in the subject is indicated. In an embodiment, if the value of the lymph index is greater than 11.3, the viral infection in the subject is indicated. In a preferred embodiment, if the value of the lymph index is greater than 11.63, the viral infection in the subject is indicated. In a more preferred embodiment, if the value of the lymph index is greater than 11.8, the viral infection in the subject is indicated. In an even more preferred embodiment, if the value of the lymph index is greater than 12.04, the viral infection in the subject is indicated. In an even more preferred embodiment, if the value of the lymph index is greater than 12.35, the viral infection in the subject is indicated. In an embodiment, if the value of LV-SD is greater than 14.41, the viral infection in the subject is indicated.

In an embodiment, the body fluid sample is whole blood.

In an embodiment, the measuring comprises measuring one or more of volume parameter, conductivity parameter, and/or light scatter parameter. In an embodiment, the measuring comprises measuring light scatter and direct current impedance from individual cells of the plurality of cells.

In an embodiment, the subject is an individual not confirmed of viral infection. In a preferred embodiment, the subject is an individual suspected of viral infection. In an embodiment, the subject is negative for viral nuclear acid testing. In an embodiment, the subject is human.

Another aspect of the invention relates to a device for identifying a subject having a viral infection, the device comprising:

1) a transducer for measuring cells passing through a flowcell; and
2) one or more processors configured to perform operations comprising:

receiving and processing measurement data from the transducer, determining one or more cell population data values based on the measuring, wherein the one or more cell population parameter data values comprise a population parameter data value from one or more of lymphocyte, neutrophil and monocyte, and determining whether or not at least one of the one or more cell population data values exceeds a predetermined threshold, wherein if at least one of the one or more cell population parameter values exceeds a predetermined threshold, the viral infection in the subject is indicated.

In an embodiment of this aspect, the viral infection is associated with upper respiratory tract illnesses. In a preferred embodiment, the viral infection is Coronavirus infection. In a more preferred embodiment, the Coronavirus is SARS-CoV-2. In an embodiment, the upper respiratory tract illness is COVID-19.

In an embodiment, the cell population data comprises one or more selected from the group consisting of monocyte distribution width (MDW), lymphocyte volume (LV), lymphocyte distribution width (LV-SD), lymphocyte conductivity (LC), lymph index, mean neutrophil volume (MNV), neutrophil distribution width (NDW), or any combinations thereof. In a preferred embodiment, the cell population data comprises MDW, and one or more of lymph index and LV-SD. In a preferred embodiment, the cell population data comprises a combination of two or more selected from the group consisting of MDW, LV, LV-SD, LC, and lymph index. In a preferred embodiment, the cell population data is a combination of MDW and one or more of LV, LV-SD, LC and lymph index. In a more preferred embodiment, the cell population data consists of MDW and lymph index. In another embodiment, the cell population data comprises or consists of MNV and NDW. The lymph index is calculated according to the following formula: lymph index=LV×(LV-SD)/LC.

In an embodiment, if the values of the MDW and the lymph index are both outside of their respective reference ranges, the viral infection in the subject is indicated.

In an embodiment, if the value of the MDW is greater than 20.27, the viral infection in the subject is indicated. In a preferred embodiment, if the value of the MDW is greater than 20.42, the viral infection in the subject is indicated. In a more preferred embodiment, if the value of the MDW is greater than 20.73, the viral infection in the subject is indicated. In an even more preferred embodiment, if the value of the MDW is greater than 21.24, the viral infection in the subject is indicated. In an embodiment, if the value of the lymph index is greater than 11.3, the viral infection in the subject is indicated. In a preferred embodiment, if the value of the lymph index is greater than 11.63, the viral infection in the subject is indicated. In a more preferred embodiment, if the value of the lymph index is greater than 11.8, the viral infection in the subject is indicated. In an even more preferred embodiment, if the value of the lymph index is greater than 12.04, the viral infection in the subject is indicated. In an even more preferred embodiment, if the value of the lymph index is greater than 12.35, the viral infection in the subject is indicated. In an embodiment, if the value of the LV-SD is greater than 14.41, the viral infection in the subject is indicated.

In an embodiment, the measuring comprises measuring one or more of volume parameter, conductivity parameter, and/or light scatter parameter. In an embodiment, the measuring comprises measuring light scatter and direct current impedance from the cells.

In an embodiment, the subject is an individual not confirmed of viral infection. In a preferred embodiment, the subject is an individual suspected of viral infection. In an embodiment, the subject is negative for viral nuclear acid testing. In an embodiment, the subject is human.

Yet another aspect of the present invention relates to a computer storage media recording an executable program for identifying a subject having a viral infection, characterized in that when the executable program is executed by a processor, the following steps are performed:

1) measuring cells passing through a flowcell;
2) determining one or more cell population parameter data values in the body fluid sample based on the measuring, wherein the one or more cell population parameter data values comprise a population parameter data value from one or more of lymphocyte, neutrophil and monocyte; and
3) determining whether or not at least one of the one or more cell population data values exceeds a predetermined threshold, wherein if at least one of the one or more cell population parameter values exceeds a predetermined threshold, the viral infection in the subject is indicated.

In an embodiment of this aspect, the viral infection is associated with upper respiratory tract illnesses. In a preferred embodiment, the viral infection is Coronavirus infection. In a more preferred embodiment, the Coronavirus is SARS-CoV-2. In an embodiment, the upper respiratory tract illness is COVID-19.

In an embodiment, the cell population data comprises one or more selected from the group consisting of monocyte distribution width (MDW), lymphocyte volume (LV), lymphocyte distribution width (LV-SD), lymphocyte conductivity (LC), lymph index, mean neutrophil volume (MNV), neutrophil distribution width (NDW), or any combinations thereof. In a preferred embodiment, the cell population data comprises MDW, and one or more of lymph index and LV-SD. In a preferred embodiment, the cell population data comprises a combination of two or more selected from the group consisting of MDW, LV, LV-SD, LC, and lymph index. In a preferred embodiment, the cell population data is a combination of MDW and one or more of LV, LV-SD, LC and lymph index. In a more preferred embodiment, the cell population data consists of MDW and lymph index. In another embodiment, the cell population data comprises or consists of MNV and NDW. The lymph index is calculated according to the following formula: lymph index=LV×(LV-SD)/LC.

In an embodiment, if one or more of the cell population data exceeds a predetermined threshold, the viral infection in the subject is indicated.

In an embodiment, if the value of the MDW is greater than 20.27, the viral infection in the subject is indicated. In a preferred embodiment, if the value of the MDW is greater than 20.42, the viral infection in the subject is indicated. In a more preferred embodiment, if the value of the MDW is greater than 20.73, the viral infection in the subject is indicated. In an even more preferred embodiment, if the value of the MDW is greater than 21.24, the viral infection in the subject is indicated. In an embodiment, if the value of the lymph index is greater than 11.3, the viral infection in the subject is indicated. In a preferred embodiment, if the value of the lymph index is greater than 11.63, the viral infection in the subject is indicated. In a more preferred embodiment, if the value of the lymph index is greater than 11.8, the viral infection in the subject is indicated. In an even more preferred embodiment, if the value of the lymph index is greater than 12.04, the viral infection in the subject is indicated. In an even more preferred embodiment, if the value of the lymph index is greater than 12.35, the viral infection in the subject is indicated. In an embodiment, if the value of LV-SD is greater than 14.41, the viral infection in the subject is indicated.

In an embodiment, the measuring comprises measuring one or more of volume parameter, conductivity parameter, and/or light scatter parameter. In an embodiment, the measuring comprises measuring light scatter and direct current impedance from the cells.

In an embodiment, the subject is an individual not confirmed of viral infection. In a preferred embodiment, the subject is an individual suspected of viral infection. In an embodiment, the subject is negative for viral nuclear acid testing. In an embodiment, the subject is human.

Definition

Some terms used herein are defined as follows. These parameters can be easily measured using commercially available instruments (such as UniCel DxH 800 Hematology Analyzer (Beckman Coulter, Brea, CA)).

| Parameter | Full name | Quantitative method |
|---|---|---|
| MDW | monocyte distribution width | Standard deviation (SD) of monocyte volume value |
| MMV | mean monocyte volume | Mean (mean) of monocyte volume value |
| MNV | mean neutrophil volume | Mean (mean) of neutrophil volume value |
| NDW | neutrophil distribution width | Standard deviation (SD) of neutrophil volume value |
| LV | lymphocyte volume | Mean (mean) of lymphocyte volume value |
| LV-SD | lymphocyte distribution width | Standard deviation (SD) of lymphocyte volume value |
| LC | lymphocyte conductivity | Mean (mean) of lymphocyte conductivity value |
| lymph index | lymph index | lymph index = LV × (LV − SD)/LC |
| WBC | White blood cell | Measured value of the instrument |
| NE | Neutrophil | Measured value of the instrument |
| LY | Lymphocyte | 仪 Measured value of the instrument |
| MO | Monocyte | Measured value of the instrument |
| NLR | Neutrophil/lymphocyte ratio | N#/L# |

BRIEF DESCRIPTION OF DRAWINGS

FIG. 2*a* shows the distribution of MDW.

DETAILED DESCRIPTION

Examples

Materials and Method

Case Selection and Data Collection

Figure 1A:
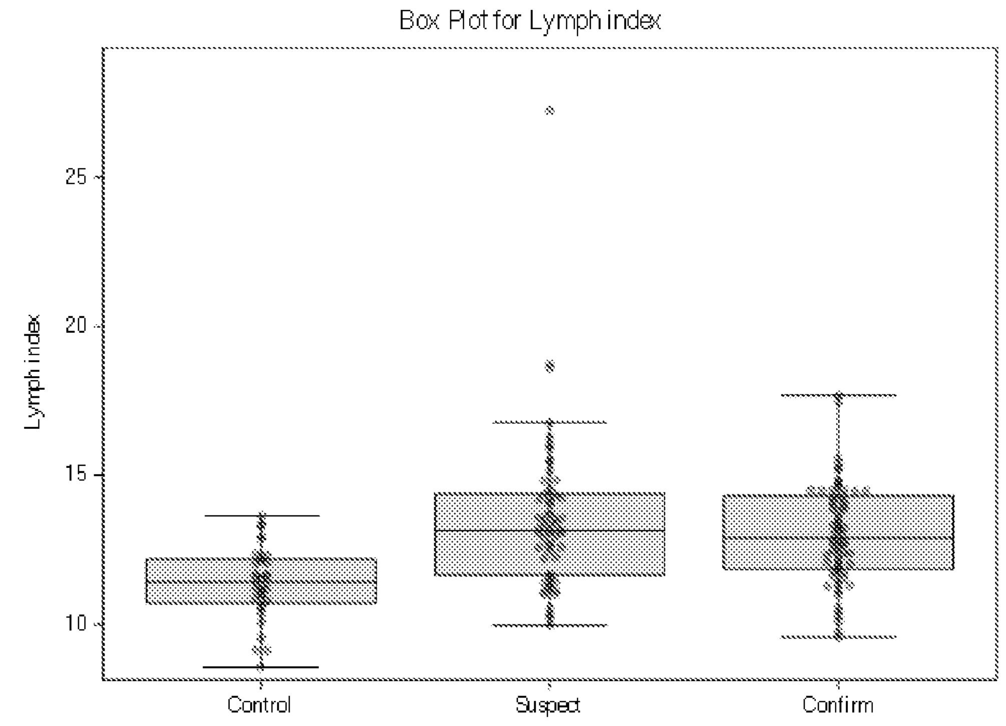
FIG. 1*a* shows the distribution of lymph index.

In this case-control study, clinical information including contact history, initial symptoms, routine hematology analysis, chest CT and RT-PCT analysis was collected from a total 128 hospitalized patients of Chinese ethnicity from Feb. 14 to 29, 2020 in The Wuhan Union Hospital, Wuhan China. Based on the criteria complied with the guideline for the diagnosis and treatment of 2019 novel coronavirus (COVID-19) infected pneumonia (sixth version), there were 96 patients (male:female ratio, 40:56) including 68 confirmed cases (contact history, clinical symptoms, CT image resembling viral infection and positive molecular testing) and 28 suspected cases (contact history, clinical symptoms, CT image resembling viral infection and negative molecular testing on admission). 32 individuals without clinical and radiological evidence of viral infection were used as controls.

Classification Criteria

Based on the criteria complied with the guideline for the diagnosis and treatment of 2019 novel coronavirus (COVID-19) infected pneumonia (sixth version), the classification indicators are as follows:

(I) Suspected Cases

Comprehensive analysis combining the following epidemiological history and clinical manifestations:

1. Epidemiology History
   - (1) A travel history or residence history in Wuhan city and surrounding areas thereof, or a travel history or residence history in other communities with case reports within 14 days before onset of illness;
   - (2) A history of contact with a patient with new Coronavirus infection (positive nucleic acid testing) within 14 days before onset of illness;
   - (3) A history of contact with a patient with fever or respiratory symptoms from Wuhan and surrounding areas thereof, or from communities with reported cases within 14 days before onset of illness;
   - (4) Clustering occurrence of ill.
2. Clinical Manifestations
   - (1) Fever and/or respiratory symptoms;
   - (2) Imaging features of new Coronavirus pneumonia;
   - (3) Normal or decreased total number of white blood cells, reduced lymphocyte count at the early stage of onset of illness.

Comply with both any one of the epidemiological history and any two of the clinical manifestations.

No clear epidemiological history, but comply with 3 of the clinical manifestations.

(II) Confirmed Cases

Suspected cases with one of the following etiological evidence:

1. Positive detection of new coronavirus nucleic acid by real-time fluorescent RT-PCR;
2. Highly homologous to known new coronaviruses by viral gene sequencing.

Cell Population Data (CPD) Analysis

All blood samples were analyzed on a UniCel DxH 800 hematology analyzer (Beckman Coulter, Brea, CA) with version 2.0 software within 4 h of collection. This instrument measures CBC with differentials as well as cell morphometric parameters including specific cell volume and distribution of cell volumes within a group of cells, such as mean neutrophil volume (MNV), neutrophil distribution width (NDW), mean monocyte volume (MMV), monocyte distribution width (MDW), mean lymphocyte volume (LV) and lymphocyte distribution width (LV-SD). A simplified lymphocyte CPD, the lymph index, was calculated as LV*LV-SD/LC (lymphocyte conductivity). In addition, 5-angle light-scattering parameters were also collected, including median-angle light scatter, upper median-angle light scatter, lower median-angle light scatter, low-angle light scatter, and axial light loss. The light scatter parameters numerically capture the morphological changes reflected by cellular complexity, granularity, and nuclear structure, with the measurement of AL2 reflecting cell size on the basis of absorbed light.

Statistical Analysis

All the analysis including ROC are performed with SAS software, the version is 9.4. Since there are total 13 variables for 3 groups for analysis. If the variables are normal distribution, we use one-way ANOVA to test the difference among 3 groups. If the variables are non-normal distribution, we use Kruskal-Wallis to test the difference among 3 groups. If the P-value is less than 0.05, we can conclude that there is a significant difference among 3 groups. Then we use Dwass-Steel-Critchlow-Fligner test for two pairwise comparisons of non-normal distribution variables, if the P-value is less than 0.05, we can conclude that there is a significant difference between 2 groups. In the end, we use Tukey's Studentized Range (HSD) test for two pairwise comparisons of normal distribution variables, if the P-value is less than 0.05, we can conclude that there is a significant difference between 2 groups.

Results

Demographic Data

Epidemiological information, clinical data, laboratory tests, and radiological characteristics were reviewed from electronic medical records. According to guideline for the diagnosis and treatment of 2019 novel coronavirus (COVID-19) infected pneumonia (sixth version), we prospectively collected and analyzed data from 128 patients (mean age 48.9 years, range 16-88 years; male:female ratio 61:67). There were 68 confirmed cases (common type), 28 suspected cases and 32 cases without clinical and radiological evidence of viral infection as controls. Among 68 confirmed cases, the male to female was 32:36; 68% (46/68) had fever and 47% (32/68) had cough. Among 28 suspected cases, the male to female was 8:20; 68% (19/28) had fever and 57% (16/28) had cough. Note: On follow-up of those suspected patients, 89% (25/28) was subsequently confirmed by positive nuclear testing with COVID-19; 11% (3/28) remained suspicious for COVID-19 infection. This shows that the method of the present disclosure can accurately identify SARS-CoV-2 infected persons at an earlier stage.

Comparison of Conventional Hematologic Parameters and CPD

Figure 1B:
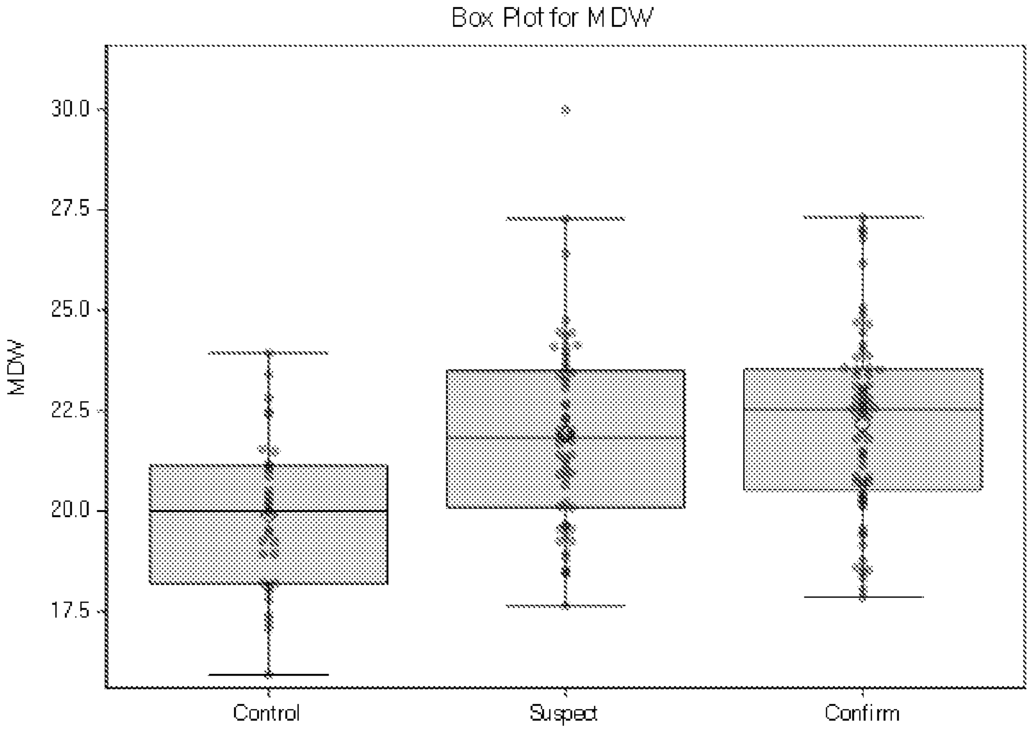
FIG. 1 shows the distribution of MDW and lymph index among the three groups (control, suspected, and confirmed).

As shown in Table 1, no statistically significant differences in conventional hematologic parameters in terms of WBC, percent neutrophils, lymphocytes, monocytes and neutrophil/lymphocyte ratio were observed among all three groups. However, the monocyte distribution width (NDW), lymphocyte distribution width (LV-SD) and lymph index (LV*LV-SD/LC) were significantly increased in both suspected and confirmed group compared to those in the controls (FIG. 1). No significant differences in NDW, LV-SD and lymph index were seen between suspected group and confirmed group. Although increase in mean lymphocyte volume (LV) and decrease in mean lymphocyte conductivity (LC) were also noted in both suspected and confirmed group, there were no statistically significant differences compared to the controls.

TABLE 1

CBC & CPD parameter in three group patients

| | Control (n = 32) Mean ± SD | Suspect (n = 28) Mean ± SD | Confirm (n = 68) Mean ±S D |
|---|---|---|---|
| MDW | 19.90 ± 1.95 | 21.71 ± 2.53 * | 22.16 ± 2.26 * * |
| MMV | 170.91 ± 8.45 | 174.39 ± 7.96 | 174.19 ± 9.10 |
| MNV | 146.47 ± 6.51 | 145.29 ± 5.28 | 143.78 ± 5.98 |
| NDW | 18.62 ± 3.24 | 17.61 ± 2.53 | 17.16 ± 1.15 |
| LV | 87.84 ± 4.23 | 88.67 ± 3.27 | 89.04 ± 4.59 |
| LV-SD | 14.62 ± 1.66 | 15.97 ± 1.56 * | 16.25 ± 1.71 * * |
| LC | 113.13 ± 7.13 | 110.71 ± 3.17 | 111.31 ± 3.23 |
| Lymph-Index | 11.36 ± 1.25 | 12.81 ± 1.55 * | 13.02 ± 1.68 * * |
| WBC | 6.54 ± 2.65 | 5.96 ± 2.61 | 5.65 ± 1.84 |

TABLE 1-continued

CBC & CPD parameter in three group patients

| | Control (n = 32) Mean ± SD | Suspect (n = 28) Mean ± SD | Confirm (n = 68) Mean ±S D |
|---|---|---|---|
| NE | 61.20 ± 11.21 | 67.77 ± 12.14 | 61.90 ± 16.21 |
| LY | 25.29 ± 9.62 | 20.66 ± 10.34 | 24.89 ± 11.61 |
| MO | 9.50 ± 2.39 | 10.16 ± 2.85 | 11.00 ± 9.73 |
| NLR | 3.37 ± 3.26 | 5.63 ± 6.53 | 3.71 ± 3.58 |

* Suspect vs Control, $p < 0.05$

* * Confirm vs Control, $p < 0.05$

The Sensitivity and the Specificity of CPD in Diagnosing COVID-19 Infection

Figure 2:
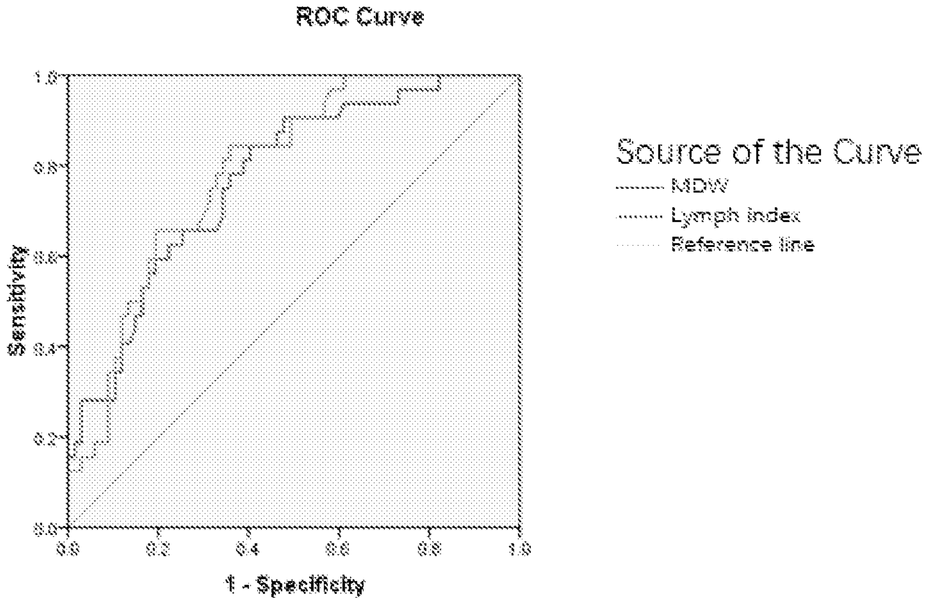
FIG. 2 shows the results of using CPD parameters to predict the diagnosis of SARS-CoV-2 infection. Among them, the control (n=32) is relative to the confirmed diagnosis (n=68).

The sensitivity and the specificity of CPD in predicting COVID-19 infection were then calculated at designated cutoff values. As indicated in Table 2, the MDW and lymph index demonstrated the best sensitivity (78.1% and 84.4%, respectively) and specificity (64.2% and 64.2%, respectively) to detect COVID-19 infection compared to other parameters. ROC curves analysis revealed that MDW and lymph index had the largest areas under the curve (AUC) of 0.77 and 0.79, respectively. With combination of MDW and lymph index, the AUC increases to 0.83 (FIG. 2, Table 2), higher than the AUC of MDW alone and the AUC of lymph index alone. This shows that the combination of MDW and lymph index can more truly reflect the possibility of the subject suffering from SARS-CoV-2 infection, compared with MDW or lymph index alone. In addition, due to different requirements for sensitivity and specificity in different application scenarios, for example, higher sensitivity is desired in the initial diagnosis and screening, and better specificity is needed in the diagnosis, we also conducted an in-depth study of the relationship between the cutoff point of MDW and lymph index and the sensitivity and specificity (Table 3). The results show that the method of the present disclosure can be better adapted to different application scenarios by adjusting the cutoff value.

TABLE 2

CPD parameter for Predicting 2019-nCoV infection

| | AUC | Cutoff Point | Sensitivity, % | Specificity, % |
|---|---|---|---|---|
| MDW | 0.772 | 20.27 | 79.41 | 59.38 |
| MMV | 0.607 | 172.5 | 65.6 | 58.2 |
| MNV | 0.397 | 144.5 | 40.6 | 51.5 |
| NDW | 0.321 | 17.23 | 34.4 | 42.4 |
| Lymph Index | 0.79 | 11.3 | 85.29 | 50 |
| NLR | 0.516 | 2.60 | 59.4 | 47.8 |
| MDW + Lymph Index | 0.831 | | 85.3 | 53.1 |

*AUC, area under the receiver operating characteristic curve.

TABLE 3

Sensitivity and specificity of MDW and lymph index

| | AUC | Cutoff Point | Sensitivity, % | Specificity, % |
|---|---|---|---|---|
| MDW | 0.7730 | 20.27[20.27, 20.29) | 79.41 | 59.38 |
| MDW | 0.7730 | 20.42[20.42, 20.63) | 75 | 62.5 |
| MDW | 0.7730 | 20.73[20.73, 20.85) | 69.12 | 65.63 |
| Lymph Index | 0.7860 | 11.3[11.3, 11.33) | 85.29 | 50 |
| Lymph Index | 0.7860 | 11.63[11.63, 11.72) | 79.41 | 59.38 |
| Lymph Index | 0.7860 | 11.8[11.8, 11.88) | 75 | 65.63 |
| Lymph Index | 0.7860 | 12.04[12.04, 12.07) | 69.12 | 68.75 |

Discussion

Circulating monocytes and lymphocytes are among the first to respond to viral infection. Several previous studies have shown that the volumetric parameters of mononuclear cells are significantly increased during various viral infections [5-7]. Therefore, volumetric increases in these immune cells have potential as viral biomarkers in humans. In current study, we have demonstrated, for the first time, lymph index and monocyte distribution width (MDW) were significantly increased in COVID-19 patients. With designated cutoff values for lymph index and MDW, we achieved the sensitivities of 84.4% and 78.1%, respectively in diagnosing COVID-19 infection. In addition, lymph index in combination with MDW demonstrates excellent diagnostic performance (AUC, 0.83), higher than the AUC with MDW alone and the AUC with lymph index alone. This shows that the combination of MDW and lymph index can more truly reflect the possibility of the subject suffering from SARS-CoV-2 infection, compared with MDW or lymph index alone. Furthermore, we show that lymph index and MDW in suspected patients, like confirmed patients were also significantly increased at the time of admission, suggesting similar pathophysiological process. It is noted that, for the 28 suspected patients tested in this example, they all have negative nucleic acid test at the time of admission, however, 25 of them (89%) were subsequently diagnosed with COVID-19 during the course of disease. This illustrates clinical significance that lymph index and MDW can be used as sensitive screening biomarkers to rapidly identify those suspected individuals before nuclear acid confirmation and to develop proper management plan. We did not see any significant changes in neutrophil volumetric parameters, MNV and NDW, at the time of admission. This is consistent with the observations of recent human studies that neutrophils mainly function as first responders during the innate immune response to acute bacterial infection or sepsis [8-10]

The whole blood cell analysis plays an important role in healthcare decision making from diagnosis through therapy and prognosis. Currently, the automated hematology analyzers are able to provide not only total leukocyte counts, but also leukocyte volumetric parameters. However, changes in leukocyte numerical parameters, such as total leukocyte count, tend to be extremely variable and nonspecific. In the case of COVID-19, total leukocytes or lymphocytes may be normal or mildly decreased, providing no definitive information for differential diagnosis. Therefore, clinical usefulness of volumetric parameters, lymph index and MDW, offers additional practical advantages. These parameters are generated during automated differential analysis without additional specimen requirements. They can be quantitative and are more accurate since significantly more leukocytes are simultaneously evaluated. Furthermore, they offer more robust turn-around-time and are more cost-effective. These volumetric parameters certainly have potential to become useful viral biomarkers to help healthcare providers in the out-patient department or fever clinic to rapidly identify those who might be infected with COVID-19 and to provide valuable information for triage decision making.

The scope of the invention is not limited by the specific embodiments described herein. In fact, from the foregoing description and drawings, various modifications of the present invention other than those described herein will be apparent to those skilled in the art. Such modifications are intended to fall within the scope of the appended claims. Furthermore, all embodiments described herein are considered to be broadly applicable and can be combined with any and all other consistent embodiments as appropriate. In addition, if prior art knowledge is not expressly incorporated by reference above, it is expressly incorporated herein in its entirety. A number of publications are cited throughout this document, and all disclosures thereof are incorporated by reference in their entirety.

The disclosures of the following references are incorporated by reference in their entirety.

REFERENCES

[1] Huang C, Wang Y, Li X, Ren L, Zhao J, Hu Y, Zhang L et al. Clinical features of patients infected with 2019 novel coronavirus in Wuhan, China. Lancet 2020; 395: 497-506

[2] Pan Y, Guan H, Zhou S, Wang Y, Li Q, Zhu T et al. Initial CT findings and temporal changes in patients with the novel coronavirus pneumonia (2019-nCoV): a study of 63 patients in Wuhan, China. European Radiology. 2020. s00330-020-06731-x

[3] Chan J F, Yuan S, Kok K H et al. A familial cluster of pneumonia associated with the 2019 novel coronavirus indicating person to person transmission: a study of a family cluster. Lancet 0.2020, 395(10223):514-523

[4] Tan W, Zhao X, Ma X et al. A novel coronavirus genome identified in a cluster of pneumonia cases-Wuhan, China 2019-2020. N Engl J Med. 2020 Feb. 20; 382(8):727-733

[5] Zhu Y, Cao X, Xu D. Detection of Morphologic Changes in Peripheral Mononuclear Cells in Hepatitis B Virus Infection Using the Beckman Coulter DXH 800. Laboratory Hematology 2011, 17:22-26

[6] JUNG Y J, KIM J H, PARK I R et al. Evaluation of cell population data on the UniCel DxH 800 Coulter Cellular Analysis system as a screening for viral infection in children. International Journal of Laboratory Hematology. 2012, 34, 283-289

[7] Zhu Y, Cao X, Tao G et al. The lymph index: a potential hematological parameter for viral infection. International Journal of Infectious Diseases 2013, 17: e490-e493

[8] Chaves F, Tierno B, Xu D. Quantitative determination of neutrophil VCS parameters by the Coulter automated hematology analyzer: new and reliable indicators for acute bacterial infection. American Journal of Clinical Pathology 2005; 124: 440-4.

[9] Chaves F, Tierno B, Xu D. Neutrophil volume distribution width: a new automated hematologic parameter for acute infection. Archive Pathology and Laboratory Medicine 2006; 130: 378-380.

[10] Xu D. Clinical applications of leukocyte morphological parameters. Int J Clin Res. 2015; 1:1.

The invention claimed is:

1. A method for identifying a subject having a viral infection, the method comprising:

flowing a body fluid sample obtained from the subject through a flowcell;

measuring individual cells of a plurality of cells in the body fluid sample;

determining one or more cell population parameter data values in the body fluid sample based on the measuring, wherein the one or more cell population parameter data values comprise a population parameter data value from one or more of lymphocyte, neutrophil or monocyte; and determining whether or not at least one of the one or more cell population parameter data values exceeds a predetermined threshold, wherein if at least one of the one or more cell population parameter data values exceeds a predetermined threshold, the viral infection in the subject is indicated and wherein the viral infection is associated with an upper respiratory tract illness or a coronavirus infection.

2. The method of claim 1, wherein the coronavirus infection is SARS-CoV-2.

3. The method of claim 1, wherein the one or more cell population parameter data values comprises one or more selected from the group consisting of monocyte distribution width (MDW), lymphocyte volume (LV), lymphocyte distribution width (LV-SD), lymphocyte conductivity (LC), lymph index, mean neutrophil volume (MNV), neutrophil distribution width (NDW), or any combinations thereof.

4. The method of claim 3, wherein the one or more cell population parameter data values comprises MDW, and one or more of lymph index or LV-SD, or wherein the cell population parameter data value comprises MNV and NDW.

5. The method of claim 3, wherein if the values of the MDW and the lymph index are both outside of their respective reference ranges, the viral infection in the subject is indicated.

6. The method of claim 3, wherein if the value of the MDW is greater than 20.27, the viral infection in the subject is indicated, or wherein if the value of the lymph index is greater than 11.3, the viral infection in the subject is indicated.

7. The method of claim 3, wherein if the value of the LV-SD is greater than 14.41, the viral infection in the subject is indicated.

8. The method of claim 1, wherein the body fluid sample is whole blood.

9. The method of claim 1, wherein the measuring comprises measuring one or more of volume parameter, conductivity parameter, or light scatter parameter, or wherein the measuring comprises measuring light scatter and direct current impedance from individual cells of the plurality of cells.

10. The method of claim 3, wherein the lymph index is calculated according to:

$$\text{lymph index} = LV \times (LV\text{-}SD)/LC.$$

11. The method of claim 1, wherein the subject is an individual not confirmed of viral infection, wherein the subject is an individual suspected of viral infection, or wherein the subject is negative for viral nucleic acid testing.

12. A method for identifying a subject having a viral infection, the method comprising:

flowing a body fluid sample obtained from the subject through a flowcell;

measuring individual cells of a plurality of cells in the body fluid sample;

determining one or more cell population parameter data values in the body fluid sample based on the measuring, wherein the one or more cell population parameter data values comprise a population parameter data value from one or more of lymphocyte, neutrophil or monocyte; and determining whether or not at least one of the one or more cell population parameter data values exceeds a predetermined threshold;

wherein if at least one of the one or more cell population parameter data values exceeds a predetermined threshold, the viral infection in the subject is indicated;

wherein the one or more cell population parameter data values comprises one or more selected from the group consisting of monocyte distribution width (MDW), lymphocyte volume (LV), lymphocyte distribution width (LV-SD), lymphocyte conductivity (LC), lymph index, mean neutrophil volume (MNV), neutrophil distribution width (NDW), or any combinations thereof; and wherein if the value of the MDW is greater than 20.27, the viral infection in the subject is indicated, or wherein if the value of the lymph index is greater than 11.3, the viral infection in the subject is indicated.

13. The method of claim 12, wherein the viral infection is associated with an upper respiratory tract illness or a coronavirus infection.

14. The method of claim 12, wherein the one or more cell population parameter data values comprises MDW, and one or more of lymph index or LV-SD, or wherein the cell population parameter data value comprises MNV and NDW;

wherein if the value of the LV-SD is greater than 14.41, the viral infection in the subject is indicated; and wherein the measuring comprises measuring one or more of volume parameter, conductivity parameter, or light scatter parameter, or wherein the measuring comprises measuring light scatter and direct current impedance from individual cells of the plurality of cells.

15. The method of claim 14, wherein the lymph index is calculated according to:

$$\text{lymph index} = LV \times (LV\text{-}SD)/LC.$$

* * * * *